United States Patent [19]
Allen

[11] Patent Number: 5,647,850
[45] Date of Patent: Jul. 15, 1997

[54] METHOD AND APPARATUS FOR VEIN LOCATION

[76] Inventor: William Ray Allen, 5418 KK Rd., Waterloo, Ill. 62298

[21] Appl. No.: 353,809

[22] Filed: Mar. 15, 1995

[51] Int. Cl.⁶ ................................................ A61H 1/00
[52] U.S. Cl. .................... 604/116; 128/DIG. 20
[58] Field of Search .............. 604/116; 128/677, 128/877, DIG. 20; 606/201, 202; 602/13, 21

[56] References Cited

U.S. PATENT DOCUMENTS

| | | |
|---|---|---|
| D. 320,858 | 10/1991 | Kida et al. |
| 3,171,410 | 3/1965 | Towle, Jr. et al. ............ 606/202 X |
| 3,242,923 | 3/1966 | Jacoby, Sr. ............ 128/DIG. 20 |
| 3,543,745 | 12/1970 | Rosenstein . |
| 3,678,926 | 7/1972 | Strittmatter ............ 602/21 |
| 3,752,147 | 8/1973 | Castbo et al. . |
| 4,182,320 | 1/1980 | Sweeney ............ 128/DIG. 20 X |
| 4,586,924 | 5/1986 | Lanning . |
| 4,664,651 | 5/1987 | Weinshenker et al. ............ 128/677 X |
| 4,671,258 | 6/1987 | Barthlome ............ 128/DIG. 20 X |
| 4,920,971 | 5/1990 | Blessinger ............ 606/202 X |
| 4,945,905 | 8/1990 | Dye et al. ............ 128/DIG. 20 X |
| 5,167,629 | 12/1992 | Vertestein . |
| 5,437,620 | 8/1995 | Shelly ............ 602/13 X |

Primary Examiner—Sam Rimell

[57] ABSTRACT

The invention described herein is a method and apparatus for vein location. The apparatus includes a vein locating device composed an inflatable bladder attached between two covers and including a holding straps for attaching the device to a limb of a human patient. The method described herein sets for the steps of placing the apparatus on the limb of a human patient and inflating the device so as to constrict veins in a desired area so as to permit the location of a particular vein or veins.

1 Claim, 3 Drawing Sheets

METHOD AND APPARATUS FOR VEIN LOCATION

BACKGROUND OF THE INVENTION

This invention is directed to a method and apparatus for vein location. Vein location is known to be problem in individuals who are suffering from shock, low blood pressure or dehydration, and is also known to become a problem in elderly patients. Inability to locate a vein can create difficulties

SUMMARY OF THE INVENTION

The object of the invention is to provide an apparatus which permits readily visible vein location in individuals where vein location may difficult. An additional object of the invention is to provide method of using the apparatus for vein location on a human patient. The objects of the invention are achieved by a device which includes a flexible bladder which is attached to a cover which includes a composite of cardboard and cloth or twill material. Once the flexible bag is attached to the composite cover system, the device may attached to a limb of a patient on a portion of the limb opposite to the side on which the desired vein is located. Inflation of the flexible bladder constricts blood flow in the given limb and thus causes the desired vein to be exposed to view.

DESCRIPTION OF THE PREFERRED EMBODIMENTS

Figure 1:
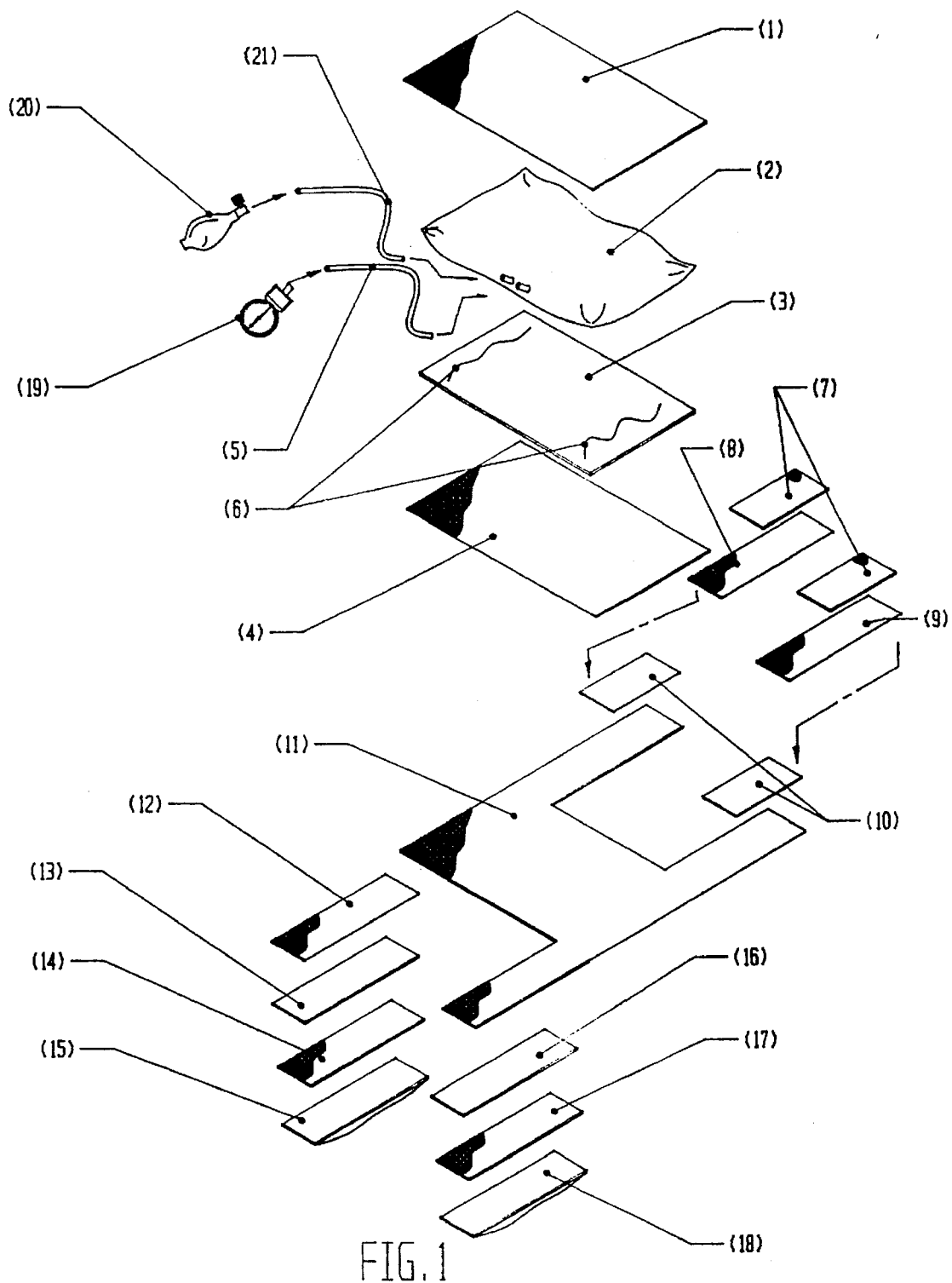
FIG. 1 discloses an exploded view of the preferred embodiment of the invention.

The preferred embodiment of the apparatus is shown in FIG. 1. An inflatable bladder (2) is sandwiched between covers (1) and (3), which are fastened together by any appropriate means, such as sewing, or by the use of adhesives. The cloth covers are formed by cotton or cotton twill material. Fastened to the inflatable bladder between the cotton covers (1,3) is a cardboard cover which adds rigidity to the system. A sphygmomanometer bulb pump (20) and pressure meter (19) are also attached to the bladder for inflation and pressure control. A lower cloth or twill cover (11) is provided which includes a central widened portion and four outlying straps. An example of the construction of the upper left hand strap is illustrated in the lower left hand portion of FIG. 1. This strap is formed by a piece of cardboard (13) which is sandwiched between pieces of cotton or twill material (12,14). Attached to the lower surface of the strap is a velcro fastener which is employed when attaching the apparatus to a human limb. Each of the straps are formed in similar fashion, except that the straps illustrated on the right side of FIG. 1 have velcro attachments on the upper surface of the strap while straps on the left side of FIG. 1 have velcro on the lower surface of the straps. The arrangement of the velcro fasteners permits complementary attachment of the two upper straps and the two lower straps together when attaching the apparatus of the preferred embodiment to a human limb.

Figure 2:
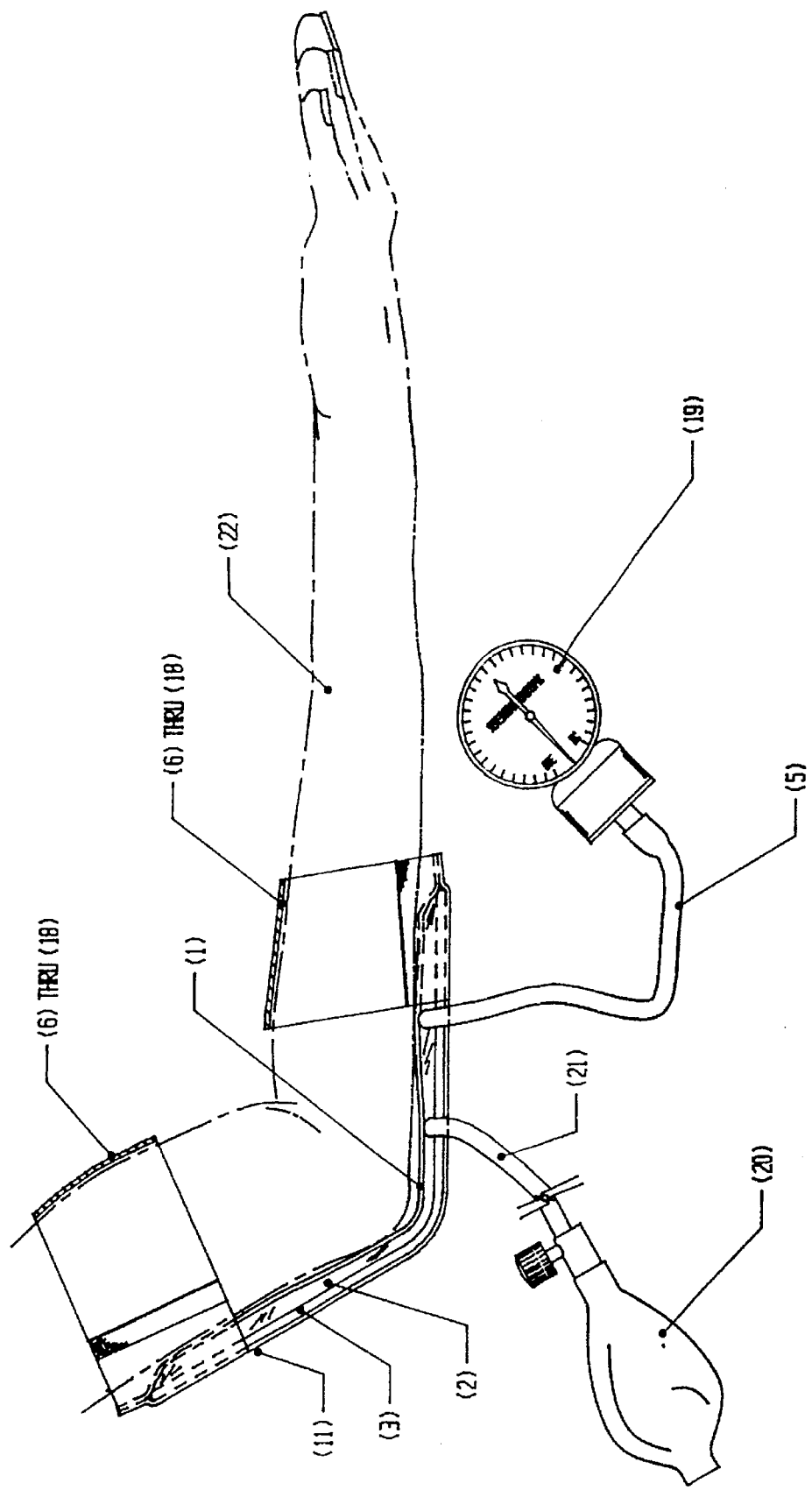
FIG. 2 discloses a side view of the preferred embodiment as applied to an elbow portion of a human arm.
Figure 3:
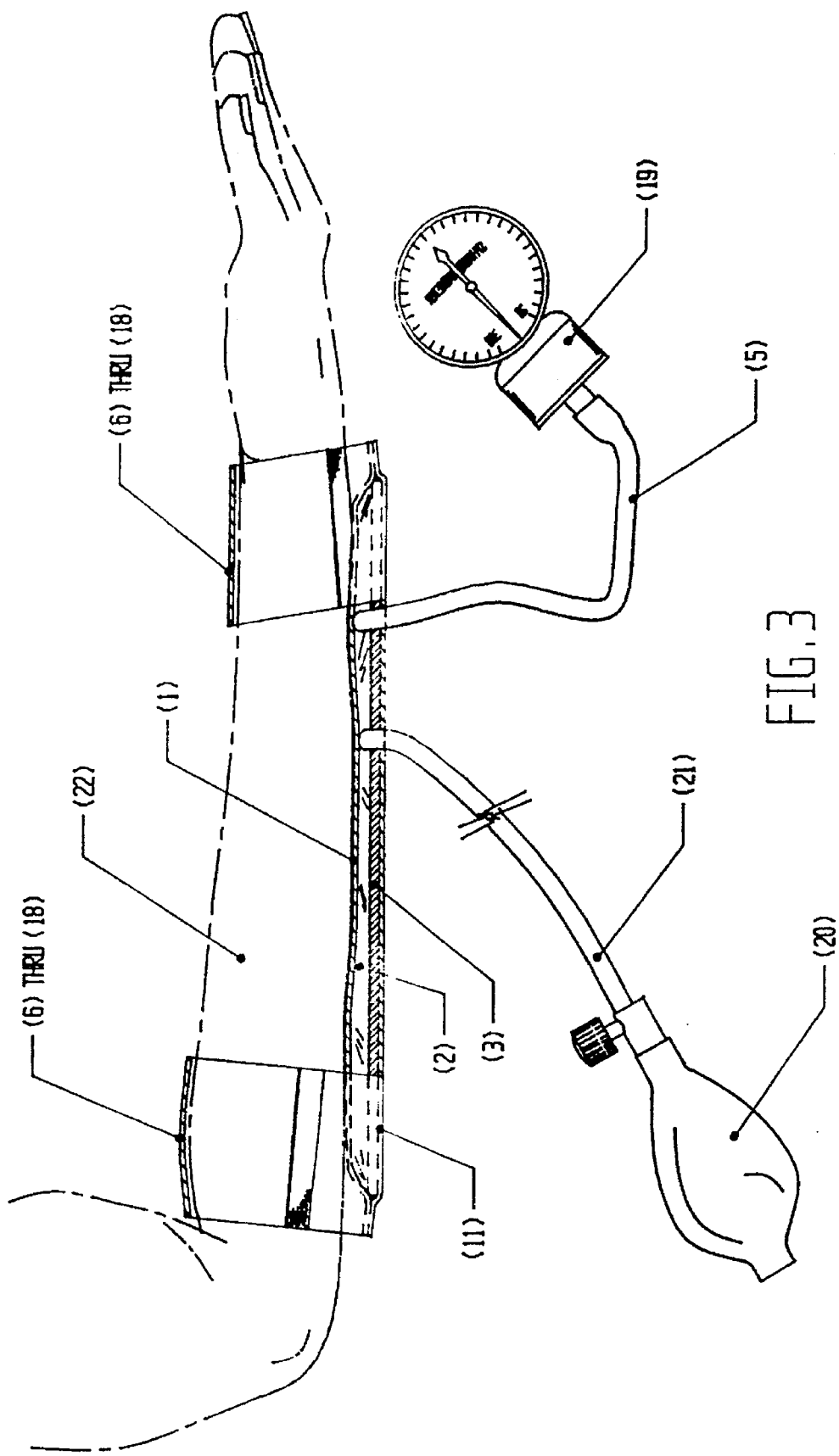
FIG. 3 discloses a side view of the preferred embodiment as applied to a non-jointed portion of a human limb.

The method of using the apparatus of FIG. 1 is illustrated in FIGS. 2 and 3. FIG. 2 illustrates the application of the apparatus to an elbow portion of a human arm while FIG. 3 illustrates a the application of the device to a human forearm. In both figures the inflatable bladder is positioned on a side of the arm opposite to the desired vein which is intended to be located. Inflation of the inflatable bladder up to a suitable pressure constricts the straps at locations adjacent to the desired vein and thus constricts the blood leaving the vein. The result of this action is that the desired vein expands and becomes visibly viewable.

I claim:

1. A method of locating a vein comprising:
   placing a vein locating device on an arm comprising:
     a relatively stiff piece of cardboard;
     an inflatable bladder attached to the upper surface of the cardboard, the inflatable bladder in fluid communication with a pumping mechanism and pressure sensing means;
     releasable straps attached to front and rear ends of the cardboard piece;
   attaching the vein locating device on a portion of a human limb opposite to a side of said limb in which said vein is located;
   inflating the vein locating device so as to constrict the blood flow in the limb until the vein is visibly viewable.

* * * * *